United States Patent
Qi et al.

(10) Patent No.: US 8,076,537 B2
(45) Date of Patent: Dec. 13, 2011

(54) METHOD OF BREEDING GERMINABLE TRANSGENIC BROADLEAVED TREE SPECIES

(75) Inventors: Liwang Qi, Beijing (CN); Shougong Zhang, Beijing (CN); Suying Han, Beijing (CN); Jianhua Wang, Beijing (CN)

(73) Assignee: The Research Institute of Forestry, Chinese Academy of Forestry, Beijing (CN)

( * ) Notice: Subject to any disclaimer, the term of this patent is extended or adjusted under 35 U.S.C. 154(b) by 541 days.

(21) Appl. No.: 12/280,516

(22) PCT Filed: Sep. 1, 2006

(86) PCT No.: PCT/CN2006/002250
§ 371 (c)(1),
(2), (4) Date: Dec. 1, 2008

(87) PCT Pub. No.: WO2007/095792
PCT Pub. Date: Aug. 30, 2007

(65) Prior Publication Data
US 2009/0260110 A1    Oct. 15, 2009

(30) Foreign Application Priority Data
Feb. 22, 2006 (CN) .......................... 2006 1 0003188

(51) Int. Cl.
A01H 1/00 (2006.01)
A01H 15/82 (2006.01)
A01H 15/87 (2006.01)
(52) U.S. Cl. ........................................ 800/294
(58) Field of Classification Search .............. 800/294, 800/278, 279, 281; 435/468, 469
See application file for complete search history.

(56) References Cited

U.S. PATENT DOCUMENTS
6,255,559 B1 * 7/2001 Cheah ........................ 800/278
2003/0192076 A1   10/2003 Kaplan et al.

FOREIGN PATENT DOCUMENTS
| CN | 1398511 A | 2/2003 |
| CN | 1582641 A | 2/2005 |
| CN | 1724654 A | 1/2006 |
| WO | WO 2005/032241 | 4/2005 |

OTHER PUBLICATIONS
International Search Report dated Nov. 29, 2006.

* cited by examiner

*Primary Examiner* — Kent L Bell
(74) *Attorney, Agent, or Firm* — Knobbe, Martens, Olson & Bear, LLP

(57) ABSTRACT

Methods of breeding germinable transgenic broadleaved tree species are disclosed which include the following steps: (1) the main stem of a tree is cutoff at the height of 50-160 cm above the ground; (2) the transection is dipped with 0.3-0.5 $OD_{600}$ of a suspension of recombinant *Agrobacterium* containing exogenous target genes for 3 minutes to 24 hours; (3) selective breeding is performed on the third day after infection by dipping the transection infected by recombinant *Agrobacterium* in step 2 with antibiotics having lethal effect on the *Agrobacterium* every other 1-2 days to obtain transgenic regeneration plants. In the practical application, the method will have the following active effects: (1) it accelerates the transfer of good exogenous genes to germinable tree species, particularly poplar and facilitates the improvement of varieties thereof; (2) it provides a new way of asexual propagation of germinable broadleaved tree species and increases the productivity and the level of intensive cultivation of germinable broadleaved tree species, so it can be used to solve the ecological problems such as vegetation restoration and to meet the requirement of the market for wood.

13 Claims, 3 Drawing Sheets

SEQUENCE LISTING

```
<160> NUMBER OF SEQ ID NOS: 3

<210> SEQ ID NO 1
<211> LENGTH: 1491
<212> TYPE: DNA
<213> ORGANISM: Artificial Sequence
<220> FEATURE:
<223> OTHER INFORMATION: Description of Artificial sequence:  BHDH probe

<400> SEQUENCE: 1
atgccgacgc ggcagctgtt tatcgacggc gagtggcgag agcccgtcca aagaaaacgc      60
attccgatca taaaccccgc caacgaacaa actattggag atattccggc agctactgct     120
gaagagatgg atattgctgt ggaagctgct cggaaagcat ttttccgtaa cagtggcaaa     180
gattggtcct cgacgactgg ggcgcatcga gccaagtatt tacgagccat tgctgcaaag     240
attaaagaca ggaaagtaga actagtggaa cttgaagcta ttgatagtgg gaaccattg      300 gaagaagcat ctttggatat ggataatgtc attggatgtt ttgagtattt tgctggcata     360
gctgaaagat tggattcaga acaaaggaca cctgtttctt taccaatgga aacgttcaag     420
tgtcatcttc taaaagaacc cattggcgtt gttggtttga tctcgccatg gaattacct      480 ctgttaatgg caatatggaa agttgcccct gccctagcat ctggatgcac tgctatactt     540
aaaccatctg aactagcatc agtaacgtgt ttggaattgg ctgaagtgtg tatggaggtg     600
ggtcttccac ctggtgtact caacattttg actggtttgg ggccagaagc tggtgctcca     660
ttggttactc atcctcatgt tgccaagatt tcatttacgg ggagtgatac tacgggagtc     720
acaattatga ctgctgctgc ccaacttgtg aaaccagtta cgttggagct tggtggaaaa     780
agcccaatcg ttgtgtttga agatgttgac cttgatacag ctgctgagtg gaccctcttc     840
ggttgctttt ggacaaatgg tcagatatgc agtgctactt ctcgactctt ggtgcatgaa     900
agcatagcga caacattctt ggagaagctt gtgaaatggt gcgagaaaat taaaatatca     960
gaccccttag aggagggttg caggcttggc cctattgtta gtcgacggca gtatgagaaa    1020
gtgatgaagt acatctcaac agctaaggag gaaggtgcca cgatcttatg tggaggtgca    1080
cgacctgagc atttagagaa aggttacttt gttcaaccaa ctattataac agacgtgaag    1140
acttccatgc aaatctggat agaggaagta tttggacctg ttctttgggt taaaacattt    1200
gcaactgaag atgaagccgt tgaactggca aatgataccc attatggtct tgctgctgca    1260
gtaatatcga aggatcttga taggtgtgag cgaatggcta aggcatttca agtcggagcc    1320
gtctgggtca actgctcaca gccttgcttc taccaagccc catggggagg caaaaagcga    1380
agtggttttg ggcgtgaact tgggaacgg ggactggaca tctacttgaa cgtaaagcag    1440
```

-continued

```
gtcacacggt atgtttctag tgagccatgg ggttggtaca agtctccttg a        1491

<210> SEQ ID NO 2
<211> LENGTH: 20
<212> TYPE: DNA
<213> ORGANISM: Artificial Sequence
<220> FEATURE:
<223> OTHER INFORMATION: Description of Artificial sequence:  P1 primer
      for BADH sequence

<400> SEQUENCE: 2
ggtagatgcg tccctgggag                                             20

<210> SEQ ID NO 3
<211> LENGTH: 21
<212> TYPE: DNA
<213> ORGANISM: Artificial Sequence
<220> FEATURE:
<223> OTHER INFORMATION: Description of Artificial sequence:  P2 primer
      for BADH sequence

<400> SEQUENCE: 3
aatctttcag caccggcaca g                                           21
```

METHOD OF BREEDING GERMINABLE TRANSGENIC BROADLEAVED TREE SPECIES

CROSS-REFERENCE TO RELATED APPLICATIONS

This application is the U.S. National Phase under 35 U.S.C. §371 of International Application PCT/CN2006/002250, filed Sep. 1, 2006, which was published in a non-English language, which claims priority to CN 200610003188.0, filed Feb. 22, 2006.

TECHNICAL FIELD

The present invention relates a method of breeding germinable transgenic broadleaved tree species with poplar as a representative.

BACKGROUND ART

Broadleaved germinable tree species is referred to a collection of arbor and half-arbor broadleaved tree species capable of regenerating new branches after cutting back, which comprises a variety of the families Salicaceae, Ulmaceae, Leguminosae, Rosaceae, Oleaceae, Betulaceae, Tiliaceae, Labiatae, Simaroubaceae, Aceraceae, Sterculiaceae, Cruciferae, Lauraceae, Plantanaceae, Scrophulariaceae, Theaceae, Meliaceae, Orchidaceae and Fagaceae and the like. Poplar, among the family Salicaceae, is the typical representative of such collection of broadleaved germinable tree species.

Poplar is the most widely-distributed tree species in the world, with the strongest adaptability. It is primarily distributed in the temperate zone and cold temperate zone of 22°- 70° north latitude, and in the regions of from low altitude to high altitude of 4800 meters.

The distribution area of poplar natural forest is about more than 20,000,000 hectares (poplar is the dominant species standing in the world natural forest), with about more than 100 species. The countries where poplar is distributed most widely are Russia, China, Canada, USA, Italy and France etc. There is a rich resource of poplars in China with the natural forest accounting for about 3,000,000 hectares and having up to 53 natural species with a wide distribution, which are ranging from *Populus suaveolens* Fisch and *Populus ussuriensis* Kom in the most northern regions of Daxing'an and Xiaoxing'an Mountains to *Populus yunnanensis* Dode in southern regions, and from *Populus euphratica* Oliv tolerant to drought and salt, to *Populus alba* Linn, to *Populus canescens* Smith etc. in areas ranging from east to west in China.

Poplar has two characteristics of early fast-growing and asexual propagation. However, there are two problems in artificial forest of China East and West as follows.

The first problem is that poplar artificial forest of Sanbei shelter forest is 4,000,000 hectares, and ⅔ of fund and labor used in Sanbei shelter forest is for the poplar development annually, which occupies 27% of forest area in the same period. The current serious problem present is: runt trees is more than 1,400,000 hectares; Longicorn beetles and *Cossidae* cause a great harm, and the counties damaged have been developed from the initial 30 to 240, with about 600,000 hectares damaged. The reasons for this problem are that deterioration of environment, not planting trees in suitable soil; and low level of intensive cultivation.

The second problem is that low productivity of eastern commercial forest, with less than 30% area of the artificial forest being capable of forming real commercial forest. The reasons are single variety, variety ageing, low productivity and low level of intensive cultivation.

Therefore, a method of breeding the plants of a germinable transgenic broadleaved tree species, particularly, those of a transgenic poplar, is needed urgently for the directional improvement of a poplar variety using genetic engineering means and to resolve the ecological problem, such as vegetation restoration etc. and the wood problem.

Plant transgenic technique is mainly by *agrobacterium* mediated transformation and gene gun mediated transformation. *Agrobacterium* mediated transformation possess the advantages of easy performance, low cost, high transformation efficiency, good repeatability, being able to introduce a large fragment of DNA, the gene introduced being incorporated with a single copy or low copies, and decreasing the occurrence of gene silence, and it is used most widely and has been used in and extended to dicotyledon economical crops, such as soybean etc. With a deeper comprehension of the mechanism of *agrobacterium* mediated transformation, the improvement on this transformation method is being made, for example, such as using strains with high invasiveness, super binary vectors, suitable explants, high efficient promoters, suitable co-transformation medium, appropriate selective agent, treatment with higher concentration of phenolic compound, such as Acetosyringone (AS), etc (Kong Y, Zhou G, Wang G, and Wang Y, 2000. Factors affecting the transformation of *Agrobacterium tumefaciens* and their applications on cereals. Chinese Journal of Applied Ecology, 11(5):791-794). Transgenic plants have been successfully obtained in monocotyledon with important values, such as rice, corn, wheat, barley etc, and specific molecular biological evidences are obtained (Hiei Y, Komari T, Kabo T., Transformation of rice mediated by *Agrobacterium tumefaciens*., Plant Mol Biol, 1997, 35:205-218; Ishida Y, Saito H, Ohta S. High efficiency transformation of maize (*Zea mays L*) mediated by *Agrobacterium tumefaciens*, Nat Biotech, 1996, 14:745-750; Cheng Ming, E. F. Joyce, Pang Shengzhi et al., Genetic transformation of wheat mediated by *Agrobacterium tumefaciens*, Plant Physiol, 1997, 115:971-980). Now, people devote to widen the scope of monocotyledon used as host of *agrobacterium* transformation and increase the transformation efficiency, for example, Chai Bao-Feng etc established the technical solution of *agrobacterium* mediated transformation in monocotyledon Kentucky Bluegrass (CHAI Bao-Feng, LIANG Ai-Hu, WANG Wei, Hu Wei, *Agrobacterium*-mediated Transformation of Kentucky Bluegrass, Acta Botanica Sinica, 2003, 45(8): 966-973).

But the key for obtaining the plants of a germinable transgenic broadleaved tree species, particularly poplar, is not the gene transformation technique, but is how to regenerate intact plants with high efficiency using the transformed cells. Therefore, the establishment of a high efficiency, practical transformation system is the important bottleneck of obtaining transgenic poplar. Up to date, examples of successful gene transformation of poplar are achieved with poplar organs using plant cell totipotency under aseptic condition. However, the difference among different varieties, different clones or individuals are relatively big, and the prior art methods often need a transgenic poplar variety and explants thereof. There is no plant regeneration technique. Exploration and research are needed on this field. This makes it unable to obtain transgenic plants of directional gene transformation for poplar needing an urgent transformation in a short term Therefore, one of the important tasks facing to the high and new technology field in today's rapid development in sciences, is how to build a simple, feasible, practicable and easy to operate transgenic regeneration technique for trees.

How to induce the production of non-embryonic tissue suitable for *agrobacterium* transformation and explore the suitable co-transformation conditions is one of the tasks of present *agrobacterium* mediated transformation of monocotyledon.

DISCLOSURE OF THE INVENTION

The aim of the present invention is to provide a method of breeding germinable transgenic broadleaved tree species, particularly poplar, with high efficiency using *agrobacterium* mediated non in vitro manipulation technique.

The method of breeding germinable transgenic broadleaved tree species provided by the present invention comprises the following steps:

(1) Cutting off the main stem of a tree, at the point of 50-160 cm above the ground surface, and make the transaction surface tidy.
(2) Infecting the transection surface with 0.3-0.5 OD600 of the suspension of recombinant *agrobacterium* carrying exogenous target gene(s) for 3 minutes to 24 hours.
(3) Selective growth and hardening using the antibiotics selection pressure is performed after infection for 12-36 hours, i.e. selective breeding is carried out by dipping the transection infected by recombinant agrobacterim in step 2 with antibiotics lethal to the *agrobacterium* every other 1-2 days to obtain germianble transgenic regeneration plants of broadleaved tree species.

To obtain a better transgenic effect in the above breeding method, the plants of a germinable broadleaved tree species being 1-3 year old is best selected.

The *agrobacterium* used for infection in Step 2 can be any kind of agrobacterim, such as EHA101, EHA105, C58c1 or LBA4404 etc, preferably LBA4404 and EHA105. Any conventional method in the genetic engineering art can be used to introduce an exogenous gene into an *agrobacterium* such as electroporation method, freeze-thaw method, etc.

The interval time in the treatment with antibiotics in step (3) is preferably 1 day; and antibiotic can be any antibiotic having toxic action or inhibitory action on the untransformed cells, such as kanamycin, ampicillin, carbenicillin, rifampicin, cefotaxime or vancomycin and the like. Additionally, if the kind of antibiotic is different, the concentration is also different. For example, the concentration of kanamycin can be 25-75 mg/L, preferably 50 mg/L; the concentration of ampicillin can be 400-600 mg/L, preferably 500 mg/L; and the concentration of rifampicin can be 100-200 mg/L, preferably 150 mg/L; etc.

Although there are a variety of germinable broadleaved tree species, very similar characteristics are shown during the transformation using the above methods. Therefore, the methods of present invention are applicable to all germinable broadleaved tree species, and particularly, very suitable for poplar. Using the above method, inflated calli form around the phloem of the incision after transformation for 5-8 days with a poplar cutting off the main stem. The type of calli will vary with the different poplar variety. After 12-20 days, buds are differentiated from the calli; and after 25-30 days, little shoots are gradually differentiated, and during the period, selection of using selective pressure of antibiotic is performed until the shoots grow into 15-25 cm-long new branches of transgenic poplar. At the same time, molecular detection and asexual propagation were performed to obtain full-grown transgenic poplar plants.

The present invention will be further illustrated in combination with the specific embodiments.

THE BEST MODE FOR CARRYING OUT THE INVENTION

The methods used in the following examples are conventional methods unless particularly indicated.

EXAMPLE 1

Breeding and Molecular Detection of Transgenic Poplar Plants

1. Breeding of Transgenic Poplar Plants

Fine polar varieties used for the starting materials include: SHY-05-HB-01 (Shanha poplar), YZY-05-HLJ (Yinzhong poplar), SLY-HB-05 (Shalan poplar), ZL-46-05 (Zhonglin 46 poplar), NM-DGY-05 (Diguo poplar), NM-CHMY-05 (Chimei poplar, SHXD-05 (Shaoxiandui poplar) and NM-XQY-05 (Xiaoqing poplar).

Figure 1:
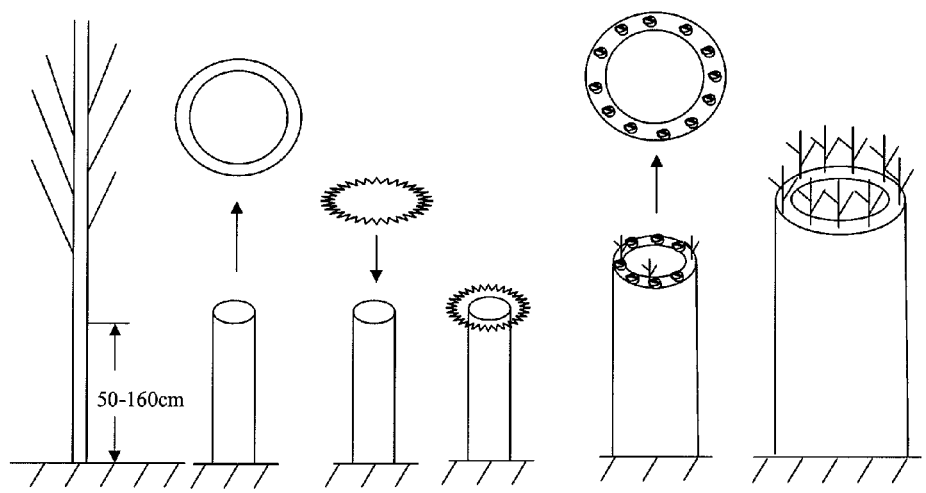
FIG. 1 is a flow diagram of breeding transgenic regeneration poplar plants using the method of present invention.
Figure 2A:
FIGS. 2A-2E are the growth process of transgenic regeneration poplar plants.
Figure 2B:
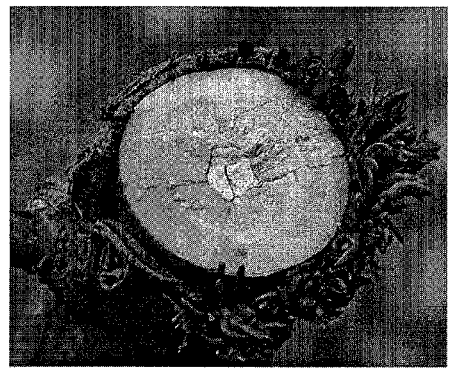
Figure 2C:
Figure 2D:
Figure 2E:

Genes DREB 1A (GenBank Accession No.: DR448909 ), BADH (GenBank Accession No.: DR448910) and SOS1 (GenBank Accession No.:AF256224) are taken for the examples. Transgenic experiments are carried out on the fine poplar varieties using the method of the present invention. The flow diagram of the method is shown in FIG. 1, which comprises the steps as follows.

(1) Genes DREB 1A, BADH and SOS1 were induced into *agrobacterium* EHA101 and LBA4404 with conventional methods of genetic engineering field respectively, and recombinants EHA101 and LBA4404 carrying DREB 1A, BADH and SOS1 respectively were obtained after selection. Untransformed strains were used as control strains (CK) and bacterial suspensions of 0.3-0.5 OD$_{600}$ thereof were prepared;
(2) Main stem of the eight poplar varieties as mentioned above, i.e. SHY-05-HB-01 (Shanha poplar), YZY-05-HLJ (Yinzhong poplar), SLY-HB-05 (Shalan poplar), ZL-46-05 (Zhonglin 46 poplar), NM-DGY-05 (Diguo poplar), NM-CHMY-05 (Chimei poplar, SHXD-05 (Shaoxiandui poplar) and NM-XQY-05 (Xiaoqing poplar) were cut off 80 cm above the ground in three groups, the first containing 196 plantlets, the second containing 18 plantlets and the third containing 58 plantlets.
(3) The transections of the cut poplar plants were infected with 0.3-0.5 OD600 of suspension of recombinant *agrobacterium* carrying exogenous target gene(s) for 4 hours.
(4) After infection, the transections infected by recombinant *agrobacterium* were dipping with 50 mg/L of kanamycin for 24 hours for selective breeding, to obtain the transgenic regeneration poplar plants. The process of regenerating transgenic plants is shown in FIGS. 2A-2E. The number of regeneration plants from different type of transformed plants, the largest number of regeneration plantlets per explant and the number of breeding big seedlings were figured out with the following statistical results shown in Table 1:

TABLE 1

In situ agrobacterium transformation of poplar stump (plantlet)

| Gene No. | The number of the explants transformed | Poplar variety | regeneration plants from the transformed plants | The most regeneration plants per explant | breeding big seedlings |
|---|---|---|---|---|---|
| EHA105 DREB 1A | 8 | SHY-05-HB-1 | 20 | 20 | 15 |
| EHA105 BADH | 8 | SHY-05-HB-1 | 25 | 2 | 4 |
| EHA105 SOS1 | 8 | SHY-05-HB-1 | 12 | 12 | 11 |
| LBA4404 DREB 1A | 8 | SHY-05-HB-1 | 2 | 2 | 7 |
| LBA4404 BADH | 8 | SHY-05-HB-1 | 13 | 10 | 9 |
| LBA4404 SOS1 | 8 | SHY-05-HB-1 | 45 | 43 | 18 |
| EHA105 DREB 1A | 8 | YZY-05-HLJ | 1 | 1 | 6 |
| EHA105 BADH | 8 | YZY-05-HLJ | 12 | 11 | 18 |
| EHA105 SOS1 | 8 | YZY-05-HLJ | 21 | 13 | 42 |
| LBA4404 DREB 1A | 8 | YZY-05-HLJ | 8 | 4 | 6 |
| LBA4404 BADH | 8 | YZY-05-HLJ | 200 | 13 | 8 |
| LBA4404 SOS1 | 8 | YZY-05-HLJ | 48 | 32 | 0 |
| CK | 1 | YZY-05-HLJ | 0 | 0 | 0 |
| EHA105 DREB 1A | 8 | SLY-HB-05 | 398 | 67 | 62 |
| EHA105 BADH | 8 | SLY-HB-05 | 100 | 28 | 47 |
| EHA105 SOS1 | 8 | SLY-HB-05 | 61 | 31 | 35 |
| LBA4404 DREB 1A | 8 | SLY-HB-05 | 58 | 58 | 38 |
| LBA4404 BADH | 8 | SLY-HB-05 | 72 | 55 | 9 |
| LBA4404 SOS1 | 8 | SLY-HB-05 | 6.625 | 30 | 6 |
| CK | 1 | SLY-HB-05 | 0 | 0 | 0 |
| EHA105 DREB 1A | 8 | ZL-46-05-A | 553 | 30 | 23 |
| EHA105 BADH | 8 | ZL-46-05-A | 64 | 6 | 6 |
| EHA105 SOSI | 8 | ZL-46-05-A | 16 | 1 | 6 |
| LBA4404 DREB 1A | 8 | ZL-46-05-A | 64 | 1 | 10 |
| LBA4404 BADH | 8 | ZL-46-05-A | 216 | 22 | 31 |
| LBA4404 SOS1 | 8 | ZL-46-05-A | 104 | 13 | 6 |
| CK | 1 | ZL-46-05-A | 0 | 0 | 6 |
| LBA4404 DREB 1A | 9 | NM-DGY-05 | 243 | 50 | 21 |
| LBA4404 SOS1 | 8 | NM-DGY-05 | 112 | 29 | 42 |
| CK | 1 | NM-DGY-05 | 0 | 0 | 0 |
| LBA4404 DREB 1A | 6 | NM-CHMY-05 | 36 | 13 | 10 |
| LBA4404 BADH | 6 | NM-CHMY-05 | 27 | 23 | 12 |
| LBA4404 SOS1 | 6 | NM-CHMY-05 | 29 | 27 | 11 |
| CK | 1 | NM-CHMY-05 | 70 | 70 | 0 |
| LBA4404 DREB 1A | 6 | NM-XQY-05 | 1 | 1 | 2 |
| LBA4404 BADH | 6 | NM-XQY-05 | 5 | 5 | 2 |
| LBA4404 SOS1 | 6 | NM-XQY-05 | 0 | 0 | 2 |
| CK | 1 | NM-XQY-05 | 31 | 31 | 0 |
| LBA4404 DREB 1A | 6 | SHXD-05 | 17 | 17 | 0 |
| LBA4404 BADH | 6 | SHXD-05 | 13 | 13 | 0 |
| LBA4404 SOS1 | 7 | SHXD-05 | 8 | 7 | 0 |
| CK | 1 | SHXD-05 | | | |

Notes:
SHY-05-HB-01 (Shanha poplar), YZY-05-HLJ (Yinzhong poplar), SLY-HB-05 (Shalan poplar), ZL-46-05 (Zhonglin 46 poplar), NM-DGY-05 (Diguo poplar), NM-CHMY-05 (Chimei poplar, SHXD-05 (Shaoxiandui poplar) and NM-XQY-05 (Xiaoqing poplar).

2. Molecular Detection of Transgenic Poplar

Taking BADH for an example, the regeneration poplar plants obtained in Step 1 are identified at molecular level using a method as follows.

Figure 3:
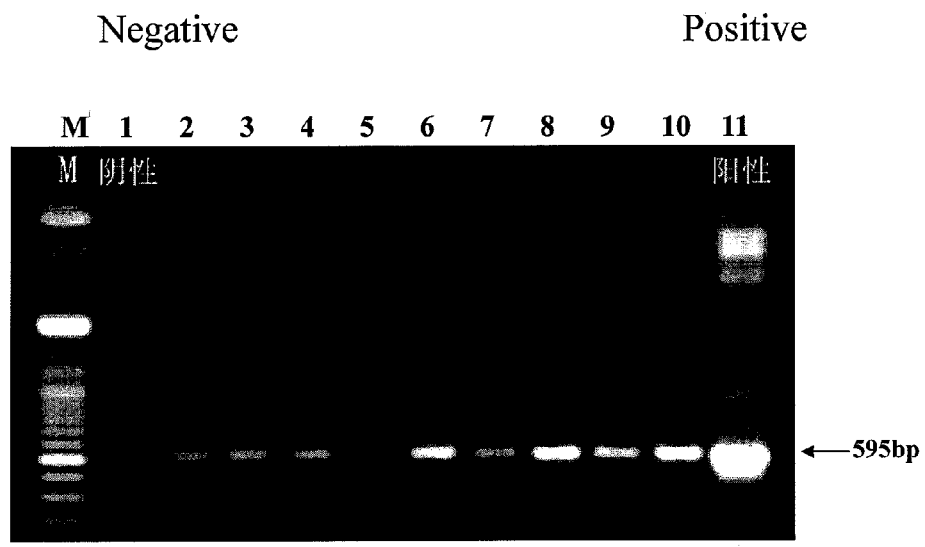
FIG. 3 shows results of detecting transgenic regeneration poplar plants by PCR amplification.

(1) Detection of BADH transgenic poplar using PCR amplification On basis of resistance selection of the regeneration plant after transformation, transgenic seedlings having a phenotype showing strong resistance to antibiotics were detected by PCR amplification. DNA was extracted from seedlings of transgenic poplar, and specific primers were designed according to known the BADH sequence as follows: P1: 5'-GGTAGATGCGTCCCTGGGAG-3' (SEQ ID NO: 2) and P2: 5'-AATCTTTCAGCACCGGCACAG-3' (SEQ ID NO: 3). The PCR amplification was carried out with primers P1 and P2 using the DNA extracted as templates. The PCR products were detected by 1.2% agarose gel electrophoresis after the reaction was over, and the results was provided in FIG. 3 (Lane M is the molecular weight marker; lane 1 is the negative control; lane 12 is the positive control; lanes 2-10 are samples for detection, wherein lane 5 is negative, lanes 2-4, 6-10 are positive). A 595bp-long DNA segment from the positive plants was PCR amplified. The transformation rate of gene BADH was figured out as 47.1%.

Figure 4:
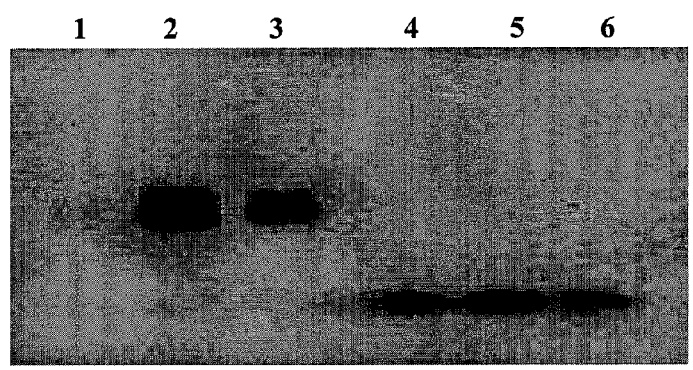
FIG. 4 shows results of identifying transgenic regeneration poplar plants by Southern Blotting assay.

(2) Identification of BADH transgenic poplar by Southern Blotting 3 of positive transgenic regeneration plants obtained in Step 1 were further detected by Southern Blotting. The sequence of BHDH probe is Sequence 1 (SEQ ID NO: 1) in the sequence listing and the results is provided in FIG. 4 (lane 1 is negative control; lane 2, 3 are positive controls;

and lanes 4-6 are samples). All the results were positive, indicating BADH had been incorporated into the genome of poplar.

The above detection results show that lots of transgenic regeneration poplar plants can be bred using the method of the present invention with a relatively high transformation rate of up to 13.4%.

INDUSTRIAL APPLICATION

The present invention provides a method of breeding plants of germinable transgenic broadleaved tree species, particularly poplar using *agrobacterium* mediated non in vitro transgenic technique with high efficiency. In practical application, the method will have the following active effects: (1) it accelerates the transfer of good exogenous gene(s) to germinable tree species, which facilitates the directional improvement of germinable broadleaved tree species; (2) it develops a new transformation method of obtaining germinable transgenic broadleaved tree species with high efficiency and increasing the possibility of transgenic success; (3) it provides a new way of asexual propagation of germinable broadleaved tree species and increases the productivity and the level of intensive cultivation of germinable broadleaved tree species, so it can be used to resolve to ecological problems such as vegetation restoration and to meet the requirement of the market for wood. Additionally, the present invention provides a theoretical basis to make clear the primary factors which affect *agrobacterium* mediated transgenic system of monocotyledon, and has an important significance in exploring and using a broader resource of *agrobacterium* mediated transgenic receptor.

What is claimed is:

1. A non in vitro method of breeding germinable transgenic broadleaved tree species, comprising the steps of:
   (1) cutting the main stem of a tree at a point 50-160 cm above the ground to form a transection;
   (2) dipping the transection in a composition comprising a suspension of recombinant *Agrobacterium* having 0.3-0.5 $OD_{600}$ comprising an exogenous target gene for 3 minutes to 24 hours;
   (3) dipping said transection infected by the recombinant *Agrobacterium* in Step 2 with antibiotics having lethal effect on the *Agrobacterium* every other 1 or 2 days, in order to obtain germinable transgenic regeneration plant of said broadleaved tree species.

2. The method according to claim 1, wherein the tree age of said germinable broadleaved tree is 1-3 years old.

3. The method according to claim 1, wherein the *Agrobacterium* used for infection is *Agrobacterium tumefaciens* selected from the group consisting of EHA101, EHA105, C58c1 or LBA4404.

4. The method according to claim 3, wherein the *Agrobacterium* is LBA4404 or EHA105.

5. The method according to claim 1, wherein the time interval for treatment with antibiotics is 1 day, and the antibiotics having lethal effect on said *Agrobacterium* are kanamycin, ampicillin, rifampicin, carbenicillin, cefotaxime or vancomycin.

6. The method according to claim 5, wherein the antibiotic is kanamycin, ampicillin or rifampicin.

7. The method according to claim 6, wherein the concentration of kanamycin is 25-75 mg/L, the concentration of ampicillin is 400-600 mg/L, or the concentration of rifampicin is 100-200 mg/L.

8. The method according to claim 7, wherein the concentration of kanamycin is 50 mg/L, the concentration of ampicillin is 500 mg/L, or the concentration of rifampicin is 150 mg/L.

9. The method according to claim 1, wherein the germinable broadleaved tree species is poplar.

10. The method according to claim 2, wherein the time interval for treatment with antibiotics is 1 day, and the antibiotics having lethal effect on said *Agrobacterium* are kanamycin, ampicillin, rifampicin, carbenicillin, cefotaxime or vancomycin.

11. The method according to claim 10, wherein the antibiotic is kanamycin, ampicillin or rifampicin.

12. The method according to claim 11, wherein the concentration of kanamycin is 25-75 mg/L, the concentration of ampicillin is 400-600 mg/L, or the concentration of rifampicin is 100-200 mg/L.

13. The method according to claim 12, wherein the concentration of kanamycin is 50 mg/L, the concentration of ampicillin is 500 mg/L, or the concentration of rifampicin is 150 mg/L.

* * * * *

UNITED STATES PATENT AND TRADEMARK OFFICE
CERTIFICATE OF CORRECTION

| | |
|---|---|
| PATENT NO. | : 8,076,537 B2 |
| APPLICATION NO. | : 12/280516 |
| DATED | : December 13, 2011 |
| INVENTOR(S) | : Qi et al. |

Page 1 of 1

It is certified that error appears in the above-identified patent and that said Letters Patent is hereby corrected as shown below:

Column 1, Line 28, "Plantanaceae," should be changed to --Platanaceae,--

Column 2, Line 65, "in a short term" should be changed to --in a short term.--

Column 3, Line 28, "agrobacterim" should be changed to --into an agrobacterium--

Column 3, Line 30, "to obtain germianble" should be changed to --to obtain germinable--

Column 3, Line 36, "kind of agrobacterim," should be changed to --kind of agrobacterium,--

Column 3, Line 39, "into an *agrobacterium*" should be changed to --into an *agrobacterium*,--

Column 5, Line 23, (Table 1), "EHA105 SOSI" should be changed to --EHA105 SOS1--

Column 6, Line 60, "of BHDH probe" should be changed to --of BADH probe--

Columns 7-8, Line 7 (Sequence Listing) "BHDH probe" should be changed to --BADH probe--

Signed and Sealed this
First Day of May, 2012

David J. Kappos
*Director of the United States Patent and Trademark Office*